(12) United States Patent
Keskinen et al.

(10) Patent No.: US 7,131,343 B2
(45) Date of Patent: Nov. 7, 2006

(54) METHOD OF MEASURING DENSITY PROPERTIES OF A PARTICLE DISTRIBUTION

(75) Inventors: Jorma Keskinen, Tampere (FI); Mikko Moisio, Tampere (FI); Marko Marjamäki, Tampere (FI); Annele Virtanen, Varalankatu (FI); Jyrki Ristimäki, Tampere (FI)

(73) Assignee: Dekati, Oy, Tampere (FI)

( * ) Notice: Subject to any disclaimer, the term of this patent is extended or adjusted under 35 U.S.C. 154(b) by 107 days.

(21) Appl. No.: 10/487,282

(22) PCT Filed: Aug. 20, 2002

(86) PCT No.: PCT/FI02/00682

§ 371 (c)(1),
(2), (4) Date: Jan. 18, 2005

(87) PCT Pub. No.: WO03/021235

PCT Pub. Date: Mar. 13, 2003

(65) Prior Publication Data

US 2005/0119836 A1 Jun. 2, 2005

(30) Foreign Application Priority Data

Aug. 20, 2001 (FI) .................................. 20011667

(51) Int. Cl.
*G01N 15/00* (2006.01)

(52) U.S. Cl. .................................... 73/865.5

(58) Field of Classification Search ............... 73/865.5, 73/28.01, 28.02, 28.03, 28.05; 324/71.4
See application file for complete search history.

(56) References Cited

U.S. PATENT DOCUMENTS 3,763,428 A * 10/1973 Preist ........................ 324/71.1
4,117,715 A    10/1978 Hoenig
4,178,796 A    12/1979 Zwicker et al.
5,296,910 A     3/1994 Cole (Continued)

FOREIGN PATENT DOCUMENTS

DE            197 33 784 A1    2/1999

(Continued)

OTHER PUBLICATIONS

Japanese Abstract, Kosaka et al., —"Particle Size Distribution Measuring Device", Japanese Application No. JP8261911 A.

(Continued)

*Primary Examiner*—Daniel S. Larkin
*Assistant Examiner*—Rodney Frank
(74) *Attorney, Agent, or Firm*—Venable LLP; Eric J. Franklin

(57) ABSTRACT

A method and a device for measuring density properies of a particle distribution, in which method a first parameter relating to the particle distribution is measured at a first measuring point (302), at least part of the flow that passed through the first measuring point is guided to the second measuring point (304), a second parameter relating to the particle distribution is measured at a second measuring point (305), and said first and second parameters relating to the particle distribution are used to determine at least one density property of the particle distribution of the original flow (306).

19 Claims, 3 Drawing Sheets

U.S. PATENT DOCUMENTS

| | | |
|---|---|---|
| 5,576,499 A | 11/1996 | Davies |
| 5,606,112 A | 2/1997 | Flagan et al. |
| 5,679,907 A * | 10/1997 | Ruck .................... 73/865.5 |
| 5,817,956 A | 10/1998 | Novick |
| 5,932,795 A | 8/1999 | Koutrakis et al. |
| 6,012,343 A | 1/2000 | Boulaud et al. |
| 6,230,572 B1 | 5/2001 | Pui et al. |
| 7,066,037 B1 * | 6/2006 | Keskinen et al. .......... 73/865.5 |

FOREIGN PATENT DOCUMENTS

| | | |
|---|---|---|
| GB | 2 344 426 A | 6/2000 |
| GB | 2 346 700 A | 8/2000 |
| WO | WO 96/06341 A3 | 2/1996 |
| WO | WO 02/18910 A1 | 3/2002 |

OTHER PUBLICATIONS

W.P. Kelly et al., Measurement of Particle Density of Inertial Classification of Differential Mobility Analyzer—Generated Monodisperse Aerosols', Aerosol Science and Technology 17(1992) pp. 199-212.

Lehtimaki et al., "A Method of Modifying the Sensitivity Function of an Aerosol Photometer", Am Ind. Hyg. Assoc., J. 49(8), (1998), pp. 396-400.

Keskinen et al., "Electrical Low Pressure Impactor", J. Aerosol Sci., vol. 23, No. 4, (1992), pp. 353-360.

* cited by examiner

METHOD OF MEASURING DENSITY PROPERTIES OF A PARTICLE DISTRIBUTION

FIELD OF THE INVENTION

The invention relates to a method and a device for measuring density properties of a particle distribution.

BACKGROUND OF THE INVENTION

With tightening environmental regulations, there is an increasing need for the measurement of particle emissions. In particular, the need for measurement is present in the development of filtering methods, in the research of various combustion processes, as well as in processes for monitoring actual emissions. One significant parameter in the measurement of particle emissions is particle density. The particle density is an important factor in a variety of properties which are significant in view of the particle being carried along, including for example the settling velocity of the particle. For this reason, the particle density is significant, for example, in the health effects of the particles, such as the accumulation of the particles in the lungs.

Problems involved in the measurement of the particle density are described, for example, in the article by W. P. Kelly and P. H. McMurry, "Measurement of Particle Density by Intertial Classification of Differential Mobility Analyzer-Generated Monodisperse Aerosol" [Aerosol Science and Technology 17: 199–212, 1992]. The same article also teaches a method of prior art for the measurement of particle density by means of a DMA device (Differential Mobility Analyzer) and an impactor. FIG. 1 shows the principle of operation of this method.

In the method disclosed in the article, a flow 13a carrying a particle distribution to be analyzed is led to an apparatus 10 consisting of a DMA device 11 and an impactor 12. The flow is first led to the DMA device 11 which, by means of an electrical field, separates the particles with a narrow electrical range of mobility from the flow to a flow 13b to be led to the impactor 12. Particles whose electrical mobility is not within this narrow range are guided with flows 13c and 13d away from the measuring device 10.

By means of the DMA device, it has thus been possible to separate the monodispersive aerosol flow 13b having a given narrow electrical mobility distribution 14b, from the polydispersive aerosol flow 13a having an electrical distribution 14a and being led to the measuring device.

This monodispersive aerosol flow is then led to the impactor 12 which, in a way known as such, classifies them on the basis of their aero-dynamic diameter, collecting particles with different aerodynamic diameters on different collection plates. By measuring the collection plates, it is possible to determine the aerodynamic size distribution 15 of the particles contained in the flow 13b input in the impactor.

When both the electrical mobility diameter and the aerodynamic size distribution of the particle distribution to be analyzed are known, it is possible to compute the density of the particle distribution in the way presented in the article.

The above-presented solution of prior art involves the problem that the density can only be determined for a narrow electrical mobility range at a time. In other words, by means of the method, the density can be computed for the monodispersive flow 13b by means of the DMA device. To determine the density distribution of the particles in the polydispersive flow 13a, this must be implemented, according to the above-presented solution of prior art, by scanning, i.e. by first determining the density in one electrical mobility range and then changing the adjustments of the DMA device in such a way that the measurement is made in another electrical mobility range. This procedure is repeated until the density has been determined in the whole range desired.

For the above-presented scanning measurement to produce reliable results, the flow 13a to be analyzed should remain unchanged during the whole measurement operation. Under real measuring conditions, there may be temporal variations in the flow to be analyzed, for which reason the above-presented solution of prior art is poorly suitable for the real-time measurement of a flow containing polydispersive particles under real conditions.

SUMMARY OF THE INVENTION

It is an aim of the method described in the present application to eliminate the above-described problems of prior art and to provide a simpler method for determining the density properties of a particle distribution.

By means of the method and device of the invention, at least one density property of the particle distribution is determined by measuring one parameter related to the particle distribution at a first measuring point and another parameter related to the particle distribution at a second measuring point. According to the invention, at least part of the flow that has passed the first measuring point is led to the second measuring point. The measured parameters are used to determine at least one density property of the particle distribution contained in the original flow.

In an embodiment of the invention, the access of particles detected at the first measuring point to the second measuring point is limited for example by using, at the first measuring point, a measuring method which removes the detected particles from the flow to be analyzed. This simplifies the need for computing.

In another embodiment of the invention, one parameter is a parameter related to the mobility of the particles, and the other is a parameter related to their aerodynamic size. For these measurements, a mobility channel analyzer and an electrical low-pressure impactor can be preferably used.

BRIEF DESCRIPTION OF THE DRAWINGS

In the following, the invention will be described in detail with reference to the appended drawings, in which.

DETAILED DESCRIPTION OF THE INVENTION

Figure 1:
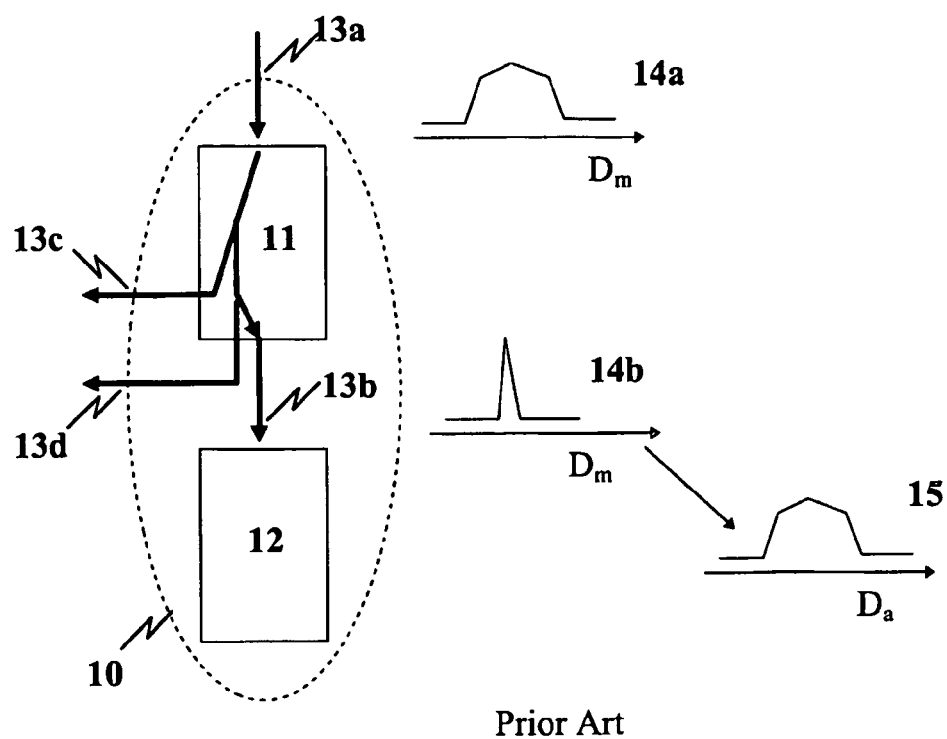
FIG. 1 shows the solution of prior art for determining the density of a particle distribution.

FIG. 1 has been discussed above in connection with the description of prior art.

Figure 2:
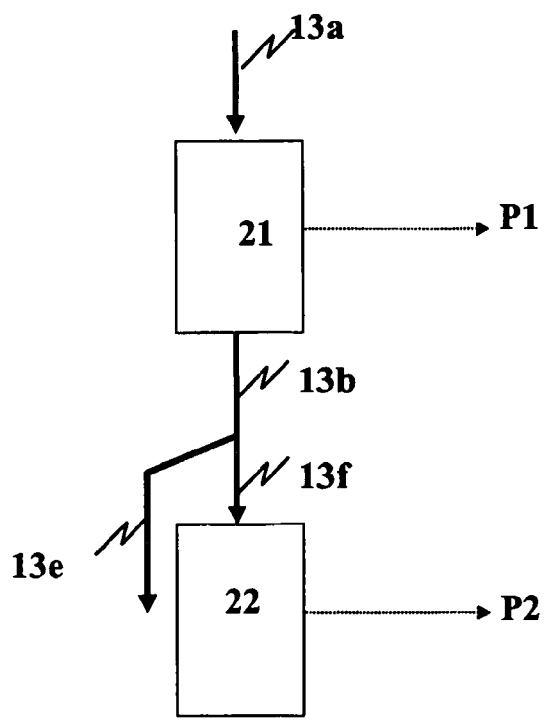
FIG. 2 shows an embodiment of the measuring device according to the invention.

FIG. 2 shows an embodiment of the measuring device according to the invention. In this embodiment, the particle distribution to be analyzed, carried by a flow 13a, is led to a first detector 21, in which at least one parameter P1 relating to the determination of the density of the particle distribution is measured from the particle distribution. The parameter P1 preferably conveys information about the electrical or mechanical mobility of the particles.

The parameter P1, as well as the second parameter P2 to be described below, can be not only single variables or other single values but also a given set of values or variables. Thus, for example, a set of three different variables produced by a measurement at the measuring point, to find out a parameter relating to a property of the particle distribution, can be considered one parameter in this context. In other words, said parameter P1 can preferably also be a set of parameters.

In an advantageous embodiment, the particles detected in a detector 21 are either collected in the detector or separated from the flow by other methods. The removal of the detected particles simplifies the computation to be made at a later step and makes it possible to execute a more versatile computation, particularly in cases in which the entire flow 13b to be led to the second detector 22 has passed through the first detector 21. In other words, it is advantageous in view of the method according to the invention that the flow 13b exiting the first detector 21 does not contain a significant quantity of such particles which were detected by the first detector 21.

Figure 4:
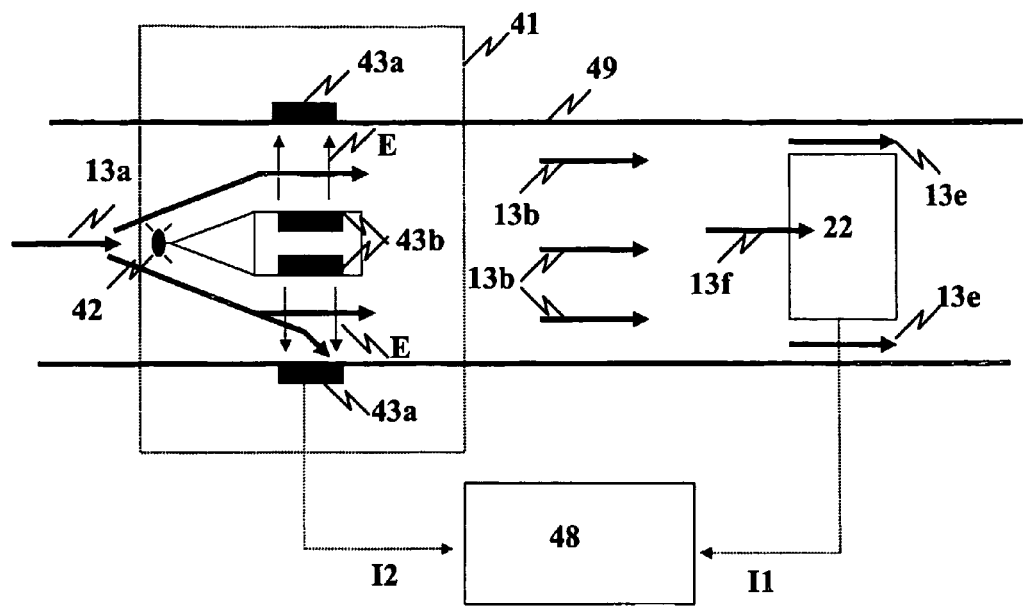
FIG. 4 shows another embodiment of the measuring device according to the invention.

The flow 13b that has passed through the first detector 21 is led to a second detector 22. Preferably, this takes place so that both measuring devices are, at least for the parts required in the detection, installed inside the same structure that guides the flow, for example a duct. FIG. 4 shows such an advantageous embodiment.

A part of the flow 13b that has passed through the first detector 21 can also be led past the second detector 22, if necessary. In FIG. 2, this is illustrated with a flow 13e. The flow 13f to be led to the second conductor 22 is preferably, for the particle distribution to be analyzed, a representative sample of the flow 13b that passed through the first detector 21. Corresponding flows are also drawn in FIG. 4.

The measurement according to the invention can be made even if the flow 13f to be led to the second detector 22 did not contain a representative sample of the flow 13b coming from the first detector 21, as long as it is possible to find out the differences between the particle distribution contained in the flow 13f to be led to the second detector 22 and the flow 13a to be analyzed. Thus, the measurement according to the invention is also possible in a situation in which a part of the flow 13a to be analyzed is guided past the first detector 21 and mixed with the flow 13b that passed the first detector 21, before the second detector 22. However, this kind of a situation is more difficult to control by computing and makes the calibration of the device more complex.

The second detector 22 produces a second measuring signal P2 which can be used to preferably determine the aerodynamic size distribution of the particles contained in the flow 13f led to the second detector 22. The density properties of the particle distribution contained in the flow 13a to be analyzed can be determined by computing on the basis of the measuring signals P1 and P2 from the first and second detectors, respectively.

In an advantageous embodiment, it is possible to compare the behaviour of the second signal P2 when the first detector 21 is turned on, with a situation in which the flow to be analyzed has free access to the second detector 22. On the basis of such a comparison, it is possible to find out the efficiency curve of the first detector 21. Such a solution makes it possible to use simpler and less expensive detectors, but on the other hand, it will make the device less suitable for real-time measurement.

According to an advantageous embodiment of the invention, the effective density of the particle distribution to be analyzed can be computed by determining the median particle size according to the mobility size ($D_m$) as well as the median particle size according to the aerodynamic size ($D_a$). When these factors are known, the effective density can be computed from the following equation:

$$D_a\sqrt{C_a\rho_a}=D_m\sqrt{C_m\rho_{\it eff}}$$

In the equation, the subindex a refers to the aerodynamic size and the subindex m to the mobility size. C is Cunningham slip correction factor, $\rho_a$ is the density corresponding to the aerodynamic size, i.e. unit density (1000 kg/m$^3$), and $\rho_{\it eff}$ is the effective density.

In an embodiment of the invention, the above-described first detector 21 is selected so that the median particle size can be determined from the first signal P1 obtained, according to the mobility size ($D_m$), and the second detector is selected so that the median particle size can be determined from the second signal according to the aerodynamic size ($D_a$). The Cunningham slip correction factors can be determined by any way known as such for a person skilled in the art, for example by table books. Thus, the only variable remaining unknown in the above equation is the effective density of the distribution to be analyzed, wherein it can be solved.

Figure 3:
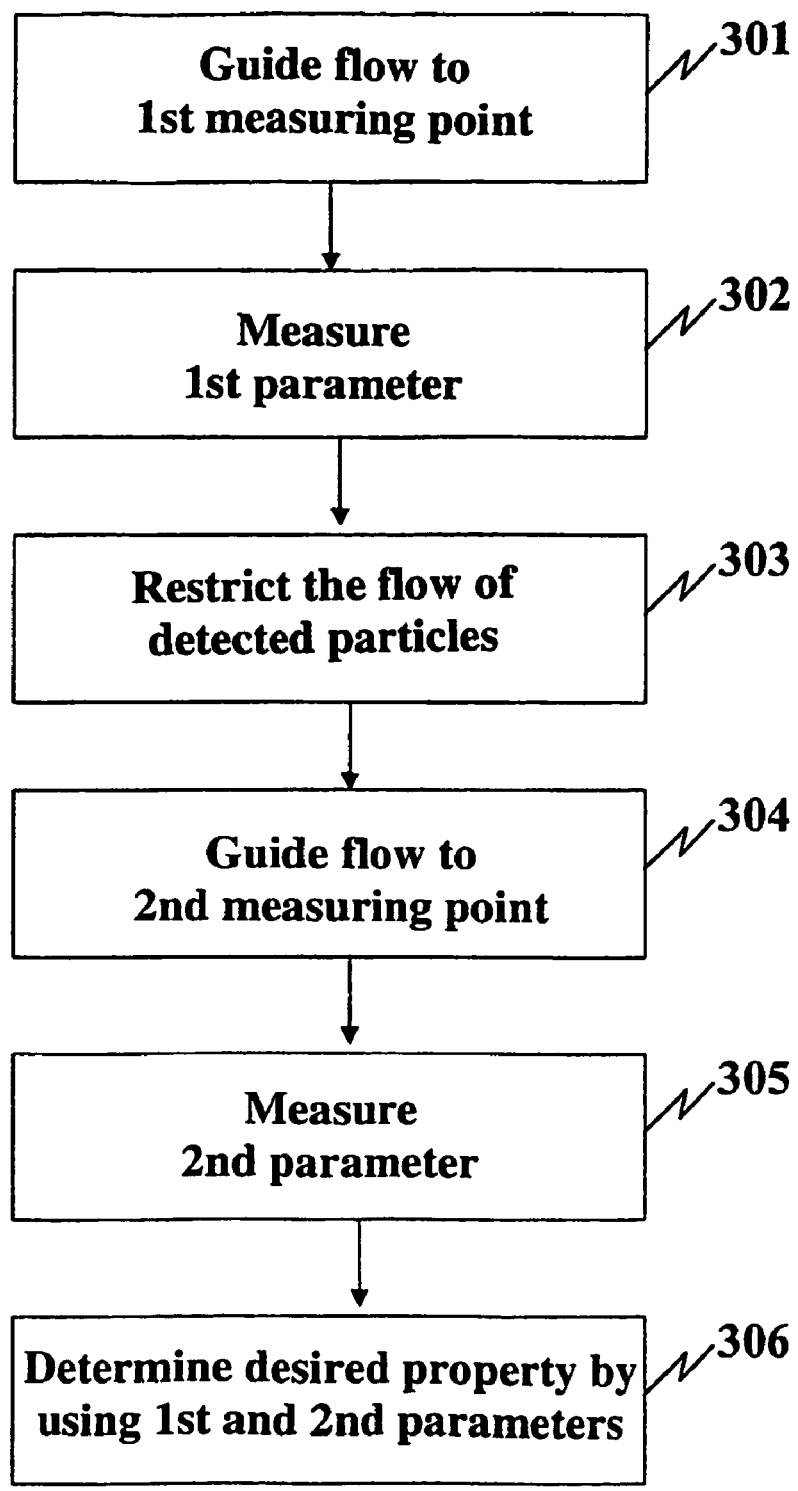
FIG. 3 shows a method according to the invention in a flow chart.

FIG. 3 shows the flow chart of a method according to the invention, which implements the above-described determination of the effective density. In the first step 301 of the method, the flow to be analyzed is led to a first measuring point where, in step 302, the first parameter relating to the particle distribution is measured at the first measuring point. The parameter may be, for example, the magnitude I2 of an electric current output by the detector, which can be used to evaluate the median particle size according to the mobility size ($D_m$).

In step 303, the access of particles measured to the first measuring point to the second measuring point is restricted. This is preferably achieved by using a collecting method of measuring, whereby the detected particles are removed from the flow under analysis in connection with the detecting process.

In step 304, at least part of the flow that has passed through the first measuring point is led to the second measuring point, where the second parameter relating to the particle distribution is measured in step 305. The parameter may be, for example, the magnitude I1 of an electric current output by the detector, which can be used to evaluate the median particle size according to the aerodynamic size ($D_m$).

In step 306, said first and second parameters relating to the particle distribution are used to determine at least one density property of the particle distribution of the original flow. To determine the effective density of the distribution, the above-presented formula can be preferably used.

FIG. 4 shows an embodiment of the solution according to the invention. In the figure, the flow 13a to be analyzed flows in a flue gas duct 49. The flow is first conducted through a mobility channel detector 41 installed in the flue gas duct. At first, the flow 13a passes a corona charger 43 which charges the particles in the flow 13a electrically. After this, the flow is introduced in an electric field E induced between electrodes 43a and 43b. By the effect of the electric field E, the electrically charged particles are carried with their charge to the electrode of the opposite sign. When hitting the electrode, the particle is discharged. This will cause a current I2 proportional to the electrical mobility of the particle distribution to be analyzed. Preferably, at least a significant part of the particles collected at the electrode are removed from the flow, for example by adhering to the electrode.

Furthermore, the flue gas duct 49 is provided with a second detector 22 which collects, in a way known as such, the particles that have passed through the mobility channel detector 41. When accumulating at the detector, the particles generate a current I1. Preferably, the second detector may also be, for example, an electrical low-pressure impactor of prior art. Another advantageous alternative is to use an electrical precipitator filter as the second detector. The advantage of the electrical low-pressure impactor in comparison with the electrical precipitator filter is, for example, the fact that the electrical low-pressure impactor can be used to measure the particle size distribution in real time, and for this reason, the above-described median particle size distribution is easy to calculate.

The current signals I1 and I2 obtained from the detectors 41 and 22 are led to a separate computing unit 48 which uses them to produce information about at least one property of the particle distribution contained in the original flow 13a.

Figure 5:
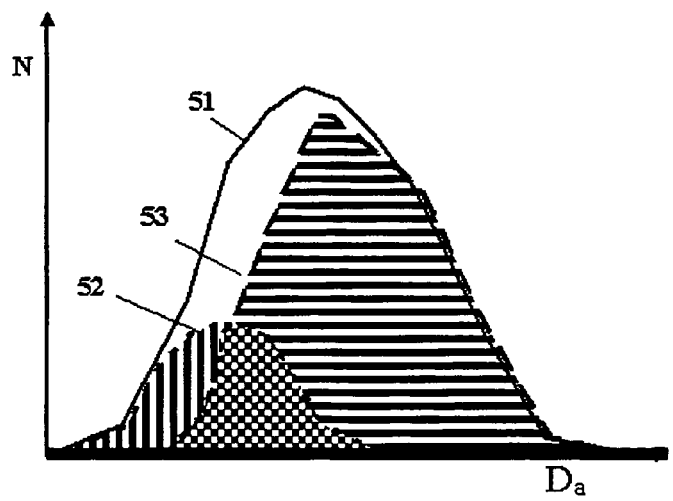
FIG. 5 illustrates the relationships between the distributions detected by different measuring devices.

FIG. 5 shows the effect of the method according to the invention on the detected particle distribution. If, in the device of FIG. 2 or 4, the second detector 22 is a detector measuring the particle size distribution, such as the above-mentioned electrical low-pressure impactor, the detector can be used to produce the particle size distribution of FIG. 5, in which the aerodynamic particle size is indicated on the horizontal axis and the quantity of detected particles is indicated on the vertical axis. If the first detector is not operating but the flow to be analyzed is guided to the detector for measuring the particle size distribution, the distribution according to the envelope curve 51 indicated by a solid line in FIG. 5 is obtained.

When the first detector 21 in FIG. 2 or the mobility detector 41 in FIG. 4 is started, the quantity of particles shown by the area limited by the dotted line 52 is removed from the particle size distribution detected by the second detector. Thus, the second detector will detect the distribution according to the broken line 53.

As stated above, it is not necessary that either of the used detectors were capable of the actual computing of the particle size distribution. It is sufficient that the detectors produce a parameter relating to the particle distribution, to be used in the computation of the desired property. In such a situation, the first detector could produce a signal which is proportional to the particle distribution detected by the first detector. For example, the first detector could produce a current signal which is proportional to the vertically hatched area remaining below the dotted curve 52 in FIG. 5. Furthermore, the second detector could produce a current signal which is proportional to the horizontally hatched area remaining below the broken line in FIG. 5.

In another embodiment, at least one of the measured parameters relating to the particle distribution contains information about at least the shape of the particle distribution measured at the second measuring point. Such parameters include, for example, standard deviation or the above-described median aerodynamic and mobility sizes.

By means of the above-described invention, the effective density of the particle distribution contained in the particle flow to be analyzed can be determined on the basis of simultaneous measurement in a large range of particle sizes. In other words, the present invention eliminates the need of so-called scanning measurement according to prior art, by replacing the classification step of prior art with the measuring step. This will make real-time measurement possible.

Hereinabove, some embodiments of the method and device according to the invention have been described, but the invention is not restricted solely to these embodiments, but it can vary within the scope of the appended claims. In particular, it has been described above that the first detector is a mobility analyzer and the second detector is either an electrical precipitator filter or an electrical low-pressure impactor. However, this arrangement is only presented as an example and it is intended to elucidate the principle of operation of the invention. In practice, under some conditions, it may be advantageous for example that the detectors are in a different order; thus, it is advantageously possible to measure the parameter relating to the aerodynamic size of the particles at the first measuring point and the parameter relating to the mobility of the particles at the second point.

The invention claimed is:

1. A method for measuring density properties of a particle distribution, in which method
   a particle flow to be analyzed is led to a first measuring point,
   particles are detected at the first measuring point with the aid of an electrical field,
   a first parameter proportional to the detected particles and relating to the particle distribution is produced,
   at least part of the flow that has passed the first measuring point is led to a second measuring point,
   a second parameter relating to the aerodynamic size of the particles is measured at the second measuring point, and
   said first and second parameters are used to determine at least one density property of the particle distribution of the original flow.

2. The method according to claim 1, in which the method is carried out in real time.

3. The method according to claim 1, in which the access of particles detected at the first measuring point to the second measuring point is restricted.

4. The method according to claim 3, in which the access of particles detected at the first measuring point to the second measuring point is restricted by using a collecting method of measuring at the first measuring point.

5. The method according to claim 1, in which at least the effective density of the particle distribution contained in the original flow is computed.

6. The method according to claim 1, in which at least one of said first and second parameter relates to the mobility of the particles.

7. The method according to claim 6, in which at least one of said first and second parameter is used for computing the median mobility size.

8. The method according to claim 6, in which said parameter relating to the mobility relates to the electrical mobility of particles.

9. The method according to claim 6, in which said parameter relating to the mobility relates to the mechanical mobility of particles.

10. The method according to claim 1, in which at least one of said first and second parameters relating to the particle distribution contains information about the shape of the measured particle distribution.

11. The method according to claim 1, in which said second parameter relating to the aerodynamic size of the particles is used for computing the median aerodynamic particle size.

12. The method according to claim 1, in which said second parameter relating to the aerodynamic size of the particles is used for computing the aerodynamic size distribution of the particle distribution.

13. The method according to claim 1, in which at least one of said first and second parameters relating to the particle distribution is measured by means of a mobility channel detector.

14. The method according to claim 1, in which at least one of said first and second parameters relating to the particle distribution is measured by means of an electrical precipitator filter.

15. The method according to claim 1, in which at least one of said first and second parameters relating to the particle distribution is measured by means of an electrical low pressure impactor.

16. A device for measuring density properties of a particle distribution, comprising means for generating an electrical field at a first measuring point,
   means for detecting particles at the first measuring point by utilizing said electrical field,
   means for producing a parameter proportional to the detected particles and relating to the mobility of the particles,
   means for measuring a second parameter relating to the aerodynamic size of the particles at the second measuring point, and
means for computing at least one density property of the original particle distribution by means of said first parameter and a parameter relating to the aerodynamic size.

17. The device according to claim 16, in which said means for measuring the parameter relating to the mobility of the particle comprise a mobility channel detector.

18. The device according to claim 16, in which said means for measuring the parameter relating to the aerodynamic size of the particle comprise an electrical precipitator filter.

19. The device according to claim 16, in which said means for measuring the parameter relating to the aerodynamic size of the particle comprise an electrical low-pressure impactor.

* * * * *